United States Patent

Behner et al.

[11] Patent Number: 4,575,501
[45] Date of Patent: Mar. 11, 1986

[54] 2-ARYLHYDRAZINO-2-THIAZOLINES, ACYL DERIVATIVES OF THESE COMPOUNDS, 2-ARYLAZO-2-THIAZOLINES, PREPARATION PROCESSES, AND THEIR USE FOR COMBATING ECTOPARASITES AND ENDOPARASITES

[75] Inventors: Otto Behner; Wilhelm Stendel; Peter Andrews, all of Wuppertal, Fed. Rep. of Germany

[73] Assignee: Bayer Aktiengesellschaft, Leverkusen, Fed. Rep. of Germany

[21] Appl. No.: 405,847

[22] Filed: Aug. 6, 1982

[30] Foreign Application Priority Data

Aug. 27, 1981 [DE] Fed. Rep. of Germany ....... 3133918

[51] Int. Cl.4 .................. C07D 277/18; A01N 43/78
[52] U.S. Cl. .................................... 514/150; 548/193; 548/195; 548/198; 514/370; 514/371; 534/795
[58] Field of Search ................ 260/158; 548/198, 195, 548/193; 424/226, 270; 514/150, 370, 371

[56] References Cited

U.S. PATENT DOCUMENTS 4,046,753  9/1977  Fisher .................................. 260/158

FOREIGN PATENT DOCUMENTS 2457309  6/1975  Fed. Rep. of Germany ...... 548/198

OTHER PUBLICATIONS

Chen, Hua, Hsueh Hsueh Pao 37, 255 (1978) abstract only.

Primary Examiner—Robert Gerstl
Attorney, Agent, or Firm—Sprung Horn Kramer & Woods

[57] ABSTRACT

2-Arylhydrazino-2-thiazolines, acyl derivatives of these compounds and 2-arylazo-2-thiazolines, of the general formula

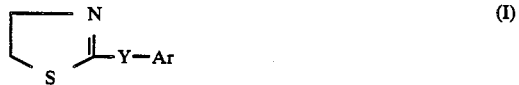

and salts thereof, are new, are prepared as described and find use for combating ectoparasites and endoparasites, such as cattle and sheep ticks, and gastric and intestinal nematodes in ruminants and carnivors.

9 Claims, No Drawings

2-ARYLHYDRAZINO-2-THIAZOLINES, ACYL DERIVATIVES OF THESE COMPOUNDS, 2-ARYLAZO-2-THIAZOLINES, PREPARATION PROCESSES, AND THEIR USE FOR COMBATING ECTOPARASITES AND ENDOPARASITES

The invention relates to certain new 2-arylhydrazino-2-thiazolines, their acyl derivatives, and 2-arylazo-2-thiazolines, to processes for their production, and to their use for combating ectoparasites and endoparasites.

It has already been disclosed that 2-phenylhydrazino-2-thiazolines monosubstituted or disubstituted in the 2,6-position in the benzene ring, 2-phenylazo-2-thiazolines and certain acyl derivatives disclose an anthelmintic, antihypertensive and ectoparasitic action (see M. T. Wu et al., Journ. pharmac. Sci, 66, 1150 (1977) and U.S. Pat. No. 4,046,753).

The present invention now provides, as new compounds, the thiazolines of the formula

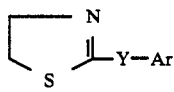   (I)

in which

Y represent —N=N— or

and $R^1$ and $R^2$ independently denote a hydrogen atom or an acyl radical, with the proviso that at least one of the substituents $R^1$ or $R^2$ represents a hydrogen atom and Ar denotes a phenyl radical which is disubstituted, or which is fused to a further ring, with the proviso that the substituents are not in the 2,6-position, or a salt thereof.

The new compounds of the present invention are outstandingly suitable for combating animal ectoparasites, in particular from the class of the acarids, and endoparasites, in particular helminthes.

According to the present invention there is further provided a process for the production of a compound of the present invention, characterised in that (a), if a compound of formula (I) is required in which Y denotes —NH—NH—, an arylhydrazine of the formula $$Ar-NH-NH_2 \quad (II)$$

in which

Ar has the meaning given above, is reacted with a thiazoline of the formula

   (III)

in which

R' denotes an optionally substituted alkyl radical, in the presence of a strong acid, or (b), if a compound of formula (I) is required in which Y denotes —NH—NH—, a thiosemicarbazide of the formula $$Ar-NH-NH-CS-NH-CH_2-CH_2-X \quad (IV)$$

in which

X denotes a hydroxyl group, an alkylsulphonyloxy or arylsulphonyloxy group, or a halogen atom, is cyclised, if appropriate in the presence of a strong acid, or (c), if a compound of formula (I) is required in which Y denotes —NH—NH—, an isothiosemicarbazide of the formula

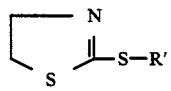   (V)

is cyclised, if appropriate in the presence of a strong acid, or (d), if a compound of formula (I) is required in which Y denotes $NR^1-NR^2$— with one of the radicals $R^1$ and $R^2$ denoting a hydrogen atom and the other denoting an acyl radical, a compound obtained by reaction variant (a), (b) or (c) is reacted with an acid halide, an acid anhydride or an isocyanate, or (e), if a compound of formula (I) is required in which Y denotes —N=N—, a compound obtained by reaction variant (a), (b) or (c) is dehydrogenated with the aid of an oxidising agent, or (f), if a compound of formula (I) is required in which Y denotes —N=N—, a compound obtained by reaction variant (d) in which the acyl radical $R^1$ or $R^2$ is a sulphonic acid radical, is subjected to a process for splitting off the sulphonyl radical as sulphinic acid; and if desired, the compound obtained by reaction variant (a), (b), (c), (d), (e) or (f) is converted into a salt thereof.

The acyl radicals of radicals $R^1$ and $R^2$ are preferably optionally substituted $C_1$ to $C_6$ alkanoyl radicals, optionally substituted $C_1$ to $C_6$ alkenoyl radicals, optionally substituted $C_7$ to $C_{10}$ aroyl radicals, $C_2$ to $C_6$ alkoxycarbonyl or carbamoyl radicals, $C_1$ to $C_6$ alkylsulphonyl radicals, or arylsulphonyl radicals which are optionally monosubstituted or polysubstituted by $C_1$ or $C_2$ alkyl groups, $NO_2$ groups or halogen. As used herein and unless otherwise specified, the term "aryl" defines preferably mono- or bi-cyclic carbocyclic aryl, such as phenyl or naphthyl.

Particularly preferred acyl radicals of radicals $R^1$ and $R^2$ are formyl, acetyl, trichloroacetyl, trifluoroacetyl, propionyl, crotonyl, benzoyl, chlorobenzoyl, ethoxycarbonyl, methoxycarbonyl, N-methylcarbamoyl, N-phenylcarbamoyl, methanesulphonyl, ethanesulphonyl, benzenesulphonyl, chlorobenzenesulphonyl, toluenesulphonyl, nitrobenzenesulphonyl or naphthalenesulphonyl radicals.

The radical Ar is preferably a phenyl radical which is disubstituted, preferably in the 2,3-position, by lower alkyl (especially $C_1$-$C_7$-lower alkyl and particularly $C_1$-$C_4$-alkyl), halogen (especially chlorine, bromine or fluorine), lower alkoxy (especially $C_1$-$C_7$-alkoxy and particularly $C_1$-$C_4$-alkoxy) or trifluoromethyl; or is naphthyl, tetrahydronaphthyl or indanyl.

The radical Ar is particularly preferably a 2,3-dimethylphenyl, 3-chloro-2-methylphenyl, 2-methoxy-3-methylphenyl, 2-methyl-3-trifluoromethylphenyl, 3-chloro-2-isopropylphenyl, 2,3-dichlorophenyl, naphth- 1-yl, 5,6,7,8-tetrahydronaphth-1-yl or indan-4-yl radical.

Preferred compounds according to the invention are those
in which
one of the radicals $R^1$ and $R^2$ denotes an optionally substituted $C_1$ to $C_6$ alkanoyl radical an optionally substituted $C_1$ to $C_6$ alkenoyl radical, a $C_7$ to $C_{10}$ aroyl, $C_2$ to $C_6$ alkoxycarbonyl or carbamoyl radical, a $C_1$ to $C_6$ alkylsulphonyl radical, or a $C_6$ to $C_{10}$ arylsulphonyl radical which is optionally monosubstituted, disubstituted or polysubstituted by $C_1$ or $C_2$ alkyl groups, nitro groups or halogen, the other one of radicals $R^1$ and $R^2$ denotes a hydrogen atom and Ar denotes a phenyl radical which is disubstituted, other than in the 2,6-position, by $C_1$ to $C_3$ alkyl, halogen, $C_1$ to $C_3$ alkoxy or —$CF_3$, or is fused to a further ring;
especially those in which the radical Ar is fused or substituted in the 2-position and 3-position.

Examples of particularly preferred compounds according to the invention are:
2-[2-(2,3-dimethylphenyl)-hydrazino]-2-thiazoline,
2-[2-(3-chloro-2-methylphenyl)-hydrazino]-2-thiazoline,
2-[2-(2-methoxy-3-methylphenyl)-hydrazino]-2-thiazoline,
2-[2-(2-methyl-3-trifluoromethylphenyl)-hydrazino]-2-thiazoline,
2-[2-(3-chloro-2-isopropylphenyl)-hydrazino]-2-thiazoline,
2-[2-(2,3-dichlorophenyl)-hydrazino]-2-thiazoline,
2-[2-(naphth-1-yl)-hydrazino]-2-thiazoline,
2-[2-(5,6,7,8-tetrahydronaphth-1-yl)-hydrazino]-2-thiazoline,
2-[2-(2,3-dimethylphenyl)-1-(or 2)-phenylsulphonylhydrazino]-2-thiazoline,
2-[2-(naphth-1-yl)-1-(or 2)-phenylsulphonylhydrazino]-2-thiazoline,
2-[2-(5,6,7,8-tetrahydronaphth-1-yl)-1-(or 2)-phenylsulphonylhydrazino]-2-thiazoline,
2-[2-(2,3-dimethylphenyl)-1-(or 2)-methylsulphonylhydrazino]-2-thiazoline,
2-[2-(indan-4-yl)-hydrazino]-2-thiazoline,
2-[2-(2,3-dimethylphenyl)-1-(or 2)-(4-chlorophenylsulphonyl)-hydrazino]-2-thiazoline,
2-[2-(2,3-dimethylphenyl)-1-(or 2)-(4-nitrophenylsulphonyl)-hydrazino]-2-thiazoline,
2-(2-(2,3-dimethylphenyl)-1-(or 2)-(4-tolylsulphonyl)-hydrazino]-2-thiazoline,
2-(2,3-dimethylphenylazo)-2-thiazoline,
2-(5,6,7,8-tetrahydro-1-naphthylazo)-2-thiazoline,
2-(1-naphthylazo)-2-thiazoline,
2-(3-chloro-2-methylphenylazo)-2-thiazoline,
2-(2,3-dichlorophenylazo)-2-thiazoline.

The thiosemicarbazides of the formula (IV) used as starting materials in reaction variant (b) are obtained in a manner known per se by reacting an isothiocyanate of the formula

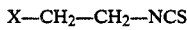   (VI)

with an arylhydrazine of the formula (II), as defined in reaction variant (a).

The isothiosemicarbazides of the formula (V) used as starting materials in reaction variant (c) are obtained in a manner known per se by reacting a thiosemicarbazide (obtained from arylhydrazines of the formula (II), as defined in reaction variant (a), and thiocyanic acid) of the formula

   (VII)

in which
Ar has the meaning given above, with, for example, 2-chloroethylamine or 2-bromoethylamine.

The acylation of reaction variant (d) is carried out in a manner known per se, for example by reacting the non-acylated compounds of formula (I) from reaction variant (a), (b) or (c), in a suitable solvent or solvent mixture in the presence of an acid acceptor, with sulphonic acid-halides, carboxylic acid-halides or anhydrides, or chloroformic acid-halides or anhydrides, or allowing the said non-acylated compound of formula (I), to react with an isocyanate in the absence of a base.

Bases employed as acid acceptors can be, for example, alkali metal or alkaline earth metal hydroxides, carbonates or bicarbonates, or tertiary amines, such as triethylamine or pyridine.

In carrying out reaction variant (e), the dehydrogenation is carried out with the aid of oxidising agents, such as minium, silver oxide, chromic acid, hydrogen peroxide, hypohalogenites or even atmospheric oxygen.

In carrying out reaction variant (f), the splitting-off process is effected, for example, even under the conditions of the synthesis of the starting compounds (i.e. under the condition of reaction variant (d)); however, it can be advantageous to carry out the reaction at an elevated temperature.

The new active compounds according to the present invention exhibit powerful acaricidal properties, especially against acarids which, as animal ectoparasites, attack domestic animals such as cattle, sheep, dogs and rabbits. At the same time the compounds according to the invention have only a low toxicity towards warm-blooded animals. They are therefore very suitable for combating animal ectoparasites from the order Acarina. In addition, however, they also possess an action against insects.

As economically important ectoparasites which play a major role especially in tropical and sub-tropical countries there may be mentioned: the Australian and South American cattle tick *Boophilus microplus*, the South African cattle tick *Boophilus decoloratus*, both from the family of the Ixodidae, and the cattle and sheep ticks of the genera Rhipicephalus, Amblyomma and Hyalomma.

In the course of time, ticks, in particular, have become resistant to the phosphoric acid esters and carbamates hitherto used as combating agents, so that the success of combating them has in many areas become increasingly dubious. To ensure economical stock raising in the infected areas there is an urgent need for agents by means of which all stages of development, that is to say larvae, nymphs, metanymphs and adults, even of resistant strains, for example of the genus Boophilus, can be combated reliably. For example, in Australia the Mackay strain, the Biarra strain and the Mount Alford strain of *Boophilus microplus* are highly resistant to the phosphoric acid esters hitherto used.

The active compounds according to the invention are equally effective both against the normally sensitive strains and the resistant strains, for example of Boophilus. When applied in the usual manner to the host animal, they act both directly against all forms parasitic on the animal and also inhibit egg production, so that the reproductive cycle of the ticks is interrupted both in the parasitic phase on the animal and in the non-parasitic phase. The laying of eggs is prevented and the development and hatching of larvae is inhibited. Aspects to be singled out particularly are the rapidly manifested excitation effect on all parasitic forms, which release their hypostome, rush around in a non-physiological manner on the host animal, drop off and finally die (detaching effect) and in particular also the good action against the metanymph stages which experience has shown to be difficult to combat.

Furthermore, they act in the same manner against all stages of development of multi-host ticks, such as Amblyomma spp., Hyalomma spp., Rhipicephalus spp., Ixodes spp., Hämaphysalis spp. and Dermacentor spp.

In addition, the new compounds of the formula (I) are also active against endoparasites. In particular, they act against gastric and intestinal nematodes in ruminants and carnivores, even those which are resistant to the customary benzimidazole anthelmintic agents and thus cannot be adequately treated therapeutically.

They act preferably against Haemonchus in particularly low dosage.

The action was examined in animal experiments after oral, subcutaneous and dermal administration to test animals heavily infested with parasites. The dosages used were tolerated very well by the test animals.

The compounds act not only after oral or parenteral administration, but also have a good action after dermal administration by means of, for example, pour on or spot-on. Thus, it is possible to employ methods of administration which are impossible in the case of the commercially available benzimidazole anthelmintic agents effective only after oral administration, but which, on the other hand, are advantageous for the user, such as, for example, dermal or subcutaneous treatment.

The new compounds can be used as anthelmintic agents both in medicine. They can be converted into the customary formulations in a known manner.

Depending on the envisaged form of administration, the new active compounds can be converted to the formulations customary in practice, such as solutions, emulsions, suspensions, powders, pastes and granules. These are prepared in a known manner, for example by mixing the active compounds with extenders, that is to say liquid, inert solvents and/or carriers, if appropriate together with surface-active agents, that is to say emulsifiers and/or dispersing agents, and, for example, when using water as the extender, organic solvents can, where appropriate, be used as auxiliary solvents.

Examples of possible solvents are: aromatic compounds (for example xylene, benzene, ortho-dichlorobenzene and trichlorobenzene), paraffins (for example petroleum fractions), alcohols, (for example methanol, ethanol, isopropanol and butanol), strongly polar organic solvents (such as dimethylformamide, N-methylpyrrolidone and dimethylsulphoxide) and also water.

Solid carriers which may be mentioned are ground natural minerals (for example kaolins, aluminas, talc and chalk) and synthetic inorganic carriers (for example highly disperse silica, and silicates); emulsifiers which may be mentioned are: both non-ionic and anionic or cationic emulsifiers, such as, for example, polyoxyethylene-fatty acid esters, polyoxyethylene-fatty alcohol esters, for example alkylaryl polyglycol ethers, alkylsulphonates and arylsulphonates, and quaternary ammonium salts with relatively long alkyl radicals. Dispersing agents which may be mentioned are: lignin, sulphite waste liquors and methylcellulose.

The formulations in general contain between 0.1 and 95% by weight of active compound, preferably between 0.5 and 90% by weight. The use concentrations are generally prepared from the said formulations by dilution with water. They can, depending on the form of use, be varied within a wide range, and are between 1 and 50,000 ppm (w/w), preferably between 5 and 500 ppm.

Application is effected in the customary manner, for example by spraying-on, pouring-on, spotting-on atomising/powdering or using a bath (dipping).

Other auxiliaries or active compounds, such as disinfectants or specifically suitable insecticides, can also be admixed to the formulations or the ready-to-use solutions.

The aqueous solutions or emulsions of the active compounds according to the invention are very stable under practical conditions, so that the ready-to-use forms for application remain active even on prolonged standing and in a pH range of 7–9 for three months or more.

The present invention also provides endoparasiticidal or ectoparasiticidal, especially anthelmintic composition containing as active ingredient a compound of the present invention in admixture with an inert pharmaceutical carrier, e.g. a solid or liquefied diluent or carrier containing a surface-active agent.

The present invention also provides a method of freeing or protecting domesticated animals from endoparasites or ectoparasites which comprises applying to said animals a compound according to the present invention, in admixture with an inert pharmaceutical diluent or carrier.

The present invention further provides domesticated animals whenever freed or protected from endoparasites or ectoparasites by the application to said animals of a compound according to the present invention, in admixture with a diluent or carrier.

PREPARATIVE EXAMPLES

Example 1

2-[2-(2,3-dimethylphenyl)-hydrazino]-2-thiazoline

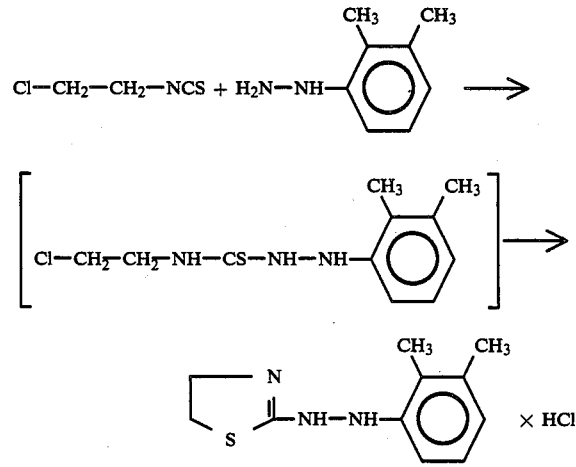

13.6 g (0.1 mol) of 2,3-dimethylphenylhydrazine were dissolved in 50 ml of toluene, and a solution of 12.8 (5% excess) of 2-chloroethyl isothiocyanate in 25 ml of toluene was added in the course of 15 minutes, while stirring and cooling with ice water, and the mixture was further stirred for 2 hours at room temperature and for 2 hours under reflux. The product was filtered off with suction when cold and was recrystallised from isopropanol. Mp. 220° to 221° (decomposition) (hydrochloride), 13.5 g (52.5% of theory).

The same compound was obtained when 2,3-dimethylphenylhydrazine and 2-methylthio-2-thiazoline hydrochloride in xylene was heated for 2 hours at 120° to 130°

Example 2

2-[2-(3-chloro-2-tolyl)-hydrazino]-2-thiazoline

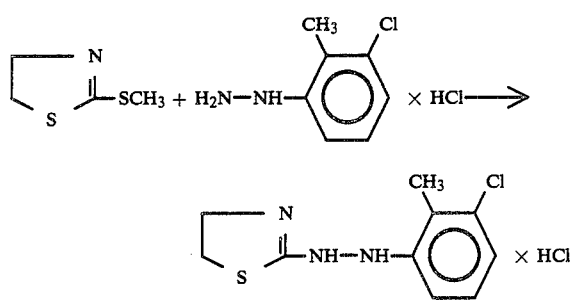

A solution of 11.2 g (5% excess) of 2-methylthio-2-thiazoline in 20 ml of isopropanol was added slowly in the course of 30 minutes to a suspension, which was stirred under reflux, of 15.5 g (0.08 mol) of 3-chloro-2-tolyl-hydrazine hydrochloride in 100 ml of isopropanol. Towards the end of the addition, a clear solution was present, from which crystallisation soon occurred anew. The mixture was stirred for a further 3 hours under reflux, and after the mixture had cooled, the prouct was filtered off under suction, rinsed with isopropanol and ether, and dried. Mp. 240° to 245° (decomposition) (hydrochloride), 21.5 g (96.5% of theory).

Example 3

2-[2-(naphth-1-yl)-hydrazino]-2-thiazoline was obtained analogously to Example 1, from naphth-1-yl-hydrazine and 2-chloroethyl isothiocyanate. Mp. 222° (decomposition) (hydrochloride).

Example 4

2-[2-(5,6,7,8-tetrahydronaphth-1-yl)-hydrazino]-2-thiazoline was obtained analogously to Example 1, from 5,6,7,8-tetrahydronaphth-1-ylhydrazine and 2-chloroethyl isothiocyanate. Mp. 238°-240° (decomposition) (hydrochloride).

Example 5

2-[2-(2,3-dimethylphenyl)-1-(or 2)-phenylsulphonylhydrazino]-2-thiazoline

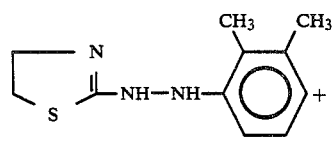

-continued

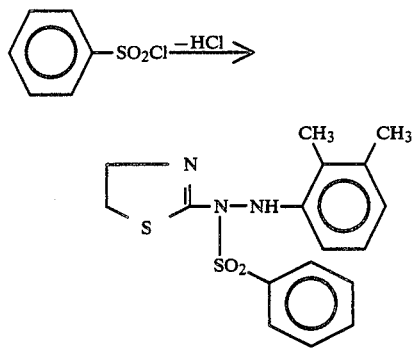

A solution of 1.94 g (10% excess) of benzenesulphonyl chloride in 10 ml of methylene chloride was added to a mixture of 2.8 g (0.01 mol) of 2-[2-(2,3-dimethylphenyl)-hydrazino]-2-thiazoline hydrochloride in 20 ml of methylene chloride and 1.2 g (0.03 mol) of sodium hydroxide in 5 ml of water in the course of 15 minutes, while stirring thoroughly. The mixture was further stirred for 1 hour at room temperature and diluted with a little water, the phases were separated, and the organic phase was dried over potassium carbonate and evaporated to dryness. The red crude product was boiled up for a short time with 15 ml of ethanol. After the mixture had been cooled and colourless crystals filtered off under suction, 2.9 g (80% of theory) mp. 121° to 124° (decomposition) were obtained.

Example 6

2-[2-(naphth-1-yl)-1-(or 2)-phenylsulphonylhydrazino]-2-thiazoline was obtained analogously to Example 5, from 2-[2-(1-naphth-1-yl)-hydrazino]-2-thiazoline and benzenesulphonyl chloride.

Example 7

2-(2,3-dimethylphenylazo)-2-thiazoline

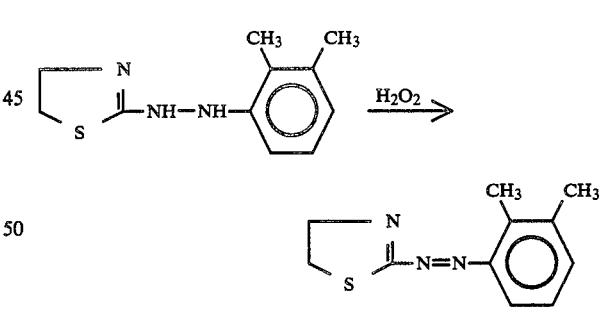

3.5 ml of 30% strength perhydrol were added to a mixture of 6.5 g (0.025 mol) of 2-[2-(2,3-dimethylphenyl)-hydrazino]-2-thiazoline hydrochloride, 60 ml of methylene chloride and 50 ml of 2N sodium hydroxide solution. The mixture was stirred for 18 hours under reflux, and a further 2 ml of perhydrol were added after 6 hours, and another 1 ml of perhydrol after 12 hours. The organic phase was separated off, dried over potassium carbonate and evaporated down, and the residue was recrystallised from hexane/diethyl ether. Mp. 74° to 79°, yield 4.1 g (74% of theory).

The dehydrogenation could also be carried out equally successfully with other oxidising agents, for example chromic acid.

Example 8

2-(3-chloro-2-tolylazo)-2-thiazoline was obtained analogously to Example 7, from 2-[2-(3-chloro-2-tolyl)-hydrazino]-2-thiazoline: mp. 96° to 102°.

Example 9

2-(5,6,7,8-tetrahydro-1-naphthylazo)-2-thiazoline was obtained analogously to Example 7, from 2-[2-(5,6,7,8-tetrahydro-naphth-1-yl)-hydrazino]-2-thiazoline.

The endoparasiticidal and ectoparasiticidal activity of compounds of this invention is illustrated by the following biotest Examples.

EXAMPLE A

Tick Test

Solvent: 35 parts by weight of ethyleneglycol monomethyl ether; 35 parts by weight of nonylphenol polyglycol ether.

To produce a suitable formulation, three parts by weight of active compound were mixed with seven parts of the abovementioned solvent/emulsifier mixture and the emulsion concentrate thus obtained was diluted with water to the particular concentration desired.

Adult, fully engorged female ticks of the species *Boophilus microplus* (resistant) were dipped for one minute into these active compound preparations. After dipping 10 female specimens, these were transferred into Petri dishes, the bottom of which was covered with a filter disc of corresponding size.

After 20 days, the activity of the active compound preparation was determined by examining the inhibition of the laying of eggs, as compared to untreated control ticks. This action was expressed as a percentage, 100% denoting that eggs were no longer laid and 0% meaning that the ticks laid normal amounts of eggs.

The active compound investigated, the concentrations tested, the parasites examined and the results obtained are given in Table 1 which follows.

TABLE 1

In-vitro test on the inhibitory action on egg-laying by ticks (*Boophilus microplus*, Biarra strain)

| Active compound | Inhibition of egg laying in ppm of active ingredient | |
|---|---|---|
| | 100% | 50% |
| chloromethiurone (known comparative preparation) [structure: Cl-phenyl(CH3)-NH-CS-N(CH3)2] | — | >5,000 |
| (compound of Example 1) [structure: thiazoline-NH-NH-xylyl] | 10,000 | 1,000 |

TABLE 1-continued

In-vitro test on the inhibitory action on egg-laying by ticks (*Boophilus microplus*, Biarra strain)

| Active compound | Inhibition of egg laying in ppm of active ingredient | |
|---|---|---|
| | 100% | 50% |
| (compound of Example 5) [structure: thiazoline-N(SO2Ph)-NH-xylyl] | >10,000 | 10,000 |
| (compound of Example 7) [structure: thiazoline-N=N-xylyl] | 300 | 200 |

EXAMPLE B

Gastric and intestinal worm test/sheep

Sheep experimentally infected with *Haemonchus contortus* were treated after the end of the pre-patency time of the parasites. The amount of active compound was administered orally as pure active compound in gelatine capsules, or was dissolved in a suitable solvent and administered subcutaneously or dermally.

The effectiveness was determined by quantitative counting of the worm eggs excreted with the faeces, before and after treatment.

Complete cessation of the excretion of eggs after the treatment meant that the worms had been expelled or were so heavily damaged that they could no longer produce any eggs (effective dose). The active compounds tested and the effective dosages (minimum effective dose) can be seen from the Table 2 which follows.

TABLE 2

| Active compound according to the invention | Method of administration | Minimum effective dose (Red ≧90%) in mg/kg |
|---|---|---|
| [structure: thiazoline-NH-NH-xylyl] | oral | 1 |
| [structure: thiazoline-N(SPh)-NH-xylyl] | oral | 1 |

TABLE 2-continued

| Active compound according to the invention | Method of administration | Minimum effective dose (Red ≧90%) in mg/kg |
|---|---|---|
| 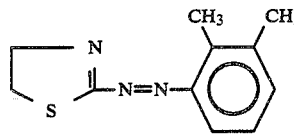 | oral | 0.5 |

What is claimed is:

1. A thiazoline derivative of the formula

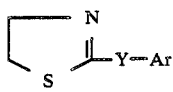

in which Y represents —N=N—

Ar denotes phenyl which is disubstituted, other than in the 2,6-position by $C_1$ to $C_3$ alkyl, halogen, $C_1$ to $C_3$ alkoxy or —$CF_3$.

2. A compound which is 2-[2-(2,3-dimethylphenyl)-1-(or 2)-phenylsulphonyl-hydrazino]-2-thiazoline.

3. A compound according to claim 1 which is 2-(2,3-dimethylphenylazo)-2-thiazoline.

4. An ectoparasiticidal or endoparasiticidal composition, which comprises an ectoparasiticidally or endoparasiticidally effective amount of a compound of claim 1 in admixture with an inert pharmaceutical carrier.

5. A composition according to claim 4, characterised in that it contains from 0.1 to 95% of the compound of claim 1, by weight.

6. A method of freeing or protecting domesticated animals from endoparasites or ectoparasites, characterised in that there is applied to said animals an ectoparasiticidally or endoparasiticidally effective amounts of compound according to claim 1, in admixture with an inert pharmaceutical carrier.

7. A method according to claim 6, characterised in that a composition is used containing from 0.1 to 95% of the active compound, by weight.

8. A method according to claim 7, characterised in that a composition is used containing from 0.5 to 90% of the active compound, by weight.

9. A compound according to claim 1, characterised in that the radical Ar is substituted in the 2-position and 3-position.

* * * * *